(12) United States Patent
Flynn (10) Patent No.: US 8,060,179 B1
(45) Date of Patent: Nov. 15, 2011

(54) BIOMAGNETIC DETECTION AND TREATMENT OF ALZHEIMER'S DISEASE

(75) Inventor: Edward R. Flynn, Albuquerque, NM (US)

(73) Assignee: Scientific Nanomedicine, Inc., Albuquerque, NM (US)

( * ) Notice: Subject to any disclaimer, the term of this patent is extended or adjusted under 35 U.S.C. 154(b) by 890 days.

(21) Appl. No.: 11/940,673

(22) Filed: Nov. 15, 2007

Related U.S. Application Data (60) Provisional application No. 60/866,095, filed on Nov. 16, 2006.

(51) Int. Cl.
*A61B 5/05* (2006.01)

(52) U.S. Cl. .................................................. 600/409

(58) Field of Classification Search .................. 600/409
See application file for complete search history.

(56) References Cited

U.S. PATENT DOCUMENTS

| | | | |
|---|---|---|---|
| 4,950,221 A | 8/1990 | Gordon | |
| 5,231,000 A | 7/1993 | Majocha et al. | |
| 5,496,534 A | 3/1996 | Klaveness et al. | |
| 6,348,185 B1 | 2/2002 | Piwnica-Worms | |
| 6,470,220 B1 | 10/2002 | Kraus | |
| 6,485,985 B1 | 11/2002 | Weitschies | |
| 6,821,504 B2 * | 11/2004 | Wisniewski et al. | ......... 424/1.69 |
| 6,997,863 B2 | 2/2006 | Handy et al. | |
| 7,074,175 B2 | 7/2006 | Handy et al. | |
| 7,081,123 B2 | 7/2006 | Merboth et al. | |
| 2002/0123079 A1 * | 9/2002 | Chen | ............................ 435/7.22 |
| 2004/0253181 A1 | 12/2004 | Port et al. | |
| 2005/0090732 A1 | 4/2005 | Ivkov et al. | |
| 2006/0093555 A1 | 5/2006 | Torres et al. | |
| 2006/0140871 A1 | 6/2006 | Sillerud | |
| 2006/0142749 A1 | 6/2006 | Ivkov | |
| 2007/0037297 A1 | 2/2007 | Yoshinaga et al. | |
| 2007/0112339 A9 | 5/2007 | Ivkov | |
| 2007/0140974 A1 | 6/2007 | Torres et al. | |
| 2007/0148095 A1 | 6/2007 | Chen et al. | |
| 2007/0166232 A1 | 7/2007 | Cho et al. | |

FOREIGN PATENT DOCUMENTS

| WO | WO01/74374 A1 | 10/2001 |
|---|---|---|
| WO | WO2007/021621 A2 | 2/2007 |

* cited by examiner

*Primary Examiner* — Jacqueline Cheng
(74) *Attorney, Agent, or Firm* — V. Gerald Grafe; Janeen Vilven (57) ABSTRACT

SQUID imaging of a subject's head after the subject having been administered superparamagnetic nanoparticles comprising: an iron-containing core, a coating covering the core and a probe molecule conjugated to the coating wherein the probe molecule locates the superparamagnetic nanoparticle to a target in the brain that is characteristic of the neurodegenerative disease; magnetizing the superparamagnetic nanoparticles using external magnetic coils; and measuring the decaying remanence magnetic fields of the superparamagnetic nanoparticles attached to the target and not from unattached superparamagnetic nanoparticles to obtain magnetic field measurements.

18 Claims, 6 Drawing Sheets

BIOMAGNETIC DETECTION AND TREATMENT OF ALZHEIMER'S DISEASE

CROSS-REFERENCE TO RELATED APPLICATIONS

This application claims priority to and the benefit of the filing of U.S. Provisional Patent Application Ser. No. 60/866,095 entitled "Biomagnetic Detection and Treatment of Alzheimer's", filed on Nov. 16, 2006, and the specifications and claims thereof are incorporated herein by reference.

INTRODUCTION

The present invention relates to a system and method for the detection and potential treatment of neurological diseases in general and such as Alzheimer's Disease specifically using superparamagnetic nanoparticles functionalized with a probe for a target associated with the neurological disease or pathophysiology associated with neurodegenerative disease.

As the population ages and lifespans continue to increase, neurodegenerative diseases of the brain are presenting challenges to the population in general and to the aging population in particular.

Alzheimer's Disease (AD) is a neurodegenerative disorder affecting approximately 2% of the population in industrialized countries and 4.5 million Americans. The financial drain on the US economy alone is $100 billion a year. The risk goes up rapidly with age and it is predicted that the rate of incidence will increase by a factor of three over the next 50 years. Delaying the onset of AD by five years would reduce the number of affected people by 50%.

At present, the only definitive diagnostic is postmortem examination of the brain with the criterion that a sufficient number of plaques be present. It is believed that plaques are extracellular deposits of fibrils and amorphous aggregates of amyloid beta-peptide (A$\beta$). Neurofibrillary tangles are intracellular fibrillar aggregates of the microtubule-associated protein tau that exhibit hyperphosphorylation and oxidative modifications and correlate with the severity of dementia in AD. The plaques are present primarily in brain regions involved with learning and memory as well in certain emotional behavior areas. The presence of plaques and tangles in association with brain regions that are damaged strongly suggests that A$\beta$ compromises the synapses and neurons and is the cause of AD. Neurofibrillary tangles occur not only in Alzheimer's disease but also in other dementia-inducing disorders. On autopsy, large numbers of these lesions are generally found in areas of the human brain important for memory and cognition.

Neurotoxic forms of A$\beta$ kill cultured neurons and are most toxic in the early stage of aggregation in the form of soluble oligomers. Animal studies show that immunization with human A$\beta$42 results in the removal of these A$\beta$ deposits with the subsequent improvement of cognition. Schenk, D., et al, *Immunization with amyloid-beta attenuates Alzheimer-disease like pathology in the PDAPP mouse*, Nature 400, p 173 (1999).

The early observation of plaques in the brain would aid the early use of these drugs and provide a longer time for the patient to be fully functional.

Certainly individuals with strong genetic susceptibility to AD would be aided by the availability of early testing for the distinguishing trademark of AD, the plaques, allowing early treatment for memory loss and consequently an increase of the quality of life. The observation and quantification of these plaques would also permit testing of new drugs to destroy the plaques as well as other therapeutic drugs of potential benefit. At the very least, knowledge of the buildup of plaques in the brain could be used by patients to change their lifestyle with regard to mental and physical stimulation, a change in diet to lower calorie and high fat input, known factors in AD susceptibility. Dietary restrictions and stimulating environments increase the resistance of neurons in the hippocampus to death, increase neurogenesis, and enhance hippocampal synaptic plasticity and neuroprotectivity.

Existing therapies based on cholinesterase inhibitors such as tacrine, donepezil, rivastigmine and galantamine would be impacted by early diagnosis.

The diagnosis of AD differentiating it from other types of dementia remains a difficult and ill-defined problem. The usual method of neuropsychological tests regarding short and long term memory and reasoning capabilities does not always successfully distinguish AD from other types of dementia which may be more amenable to treatment.

Recent research on detection using positron emission tomography (PET) and magnetic resonance imaging (MRI) are not definitive and are quite expensive.

Early detection of the buildup of A$\beta$ and tau will be a definitive diagnostic of AD and would provide a measure of the progress of the disease and the efficacy of treatment. Although A$\beta$ and tau occur in normal brains, they have a much higher density in AD patients. The relevant dividing line between normal and AD patients is important to identify and a new methodology is required. An inexpensive, less invasive, and more definitive method for determining the presence of AD is highly desired and may also permit a method for targeted treatment.

Plaques are found in AD and certain other neurological diseases such as Lewybody Parkinson's Disease and Creuzfeld-Jacob variant, a prion disease. Although the definitive diagnosis of AD is the post-mortem count of these plaques, an improved method of early detection of such plaques in living subjects would provide a diagnosis of AD versus other dementias and the possibility of early treatment.

SUMMARY OF THE INVENTION

One embodiment of the present invention provides a method for in-vivo detection of neurodegenerative disease in the brain comprising SQUID imaging of a subject's head after the subject having been administered superparamagnetic nanoparticles comprising an iron-containing core, a coating covering the core and a probe molecule conjugated to the coating wherein the probe molecule locates the superparamagnetic nanoparticle to a target in the brain that is characteristic of the neurodegenerative disease. The superparamagnetic nanoparticles are magnetized using external magnetic coils. The decaying remanence magnetic fields of the superparamagnetic nanoparticles attached to the target and not from unattached superparamagnetic nanoparticles are measured to obtain magnetic field measurements.

Another embodiment of the present invention is a method for in-vivo detection of Alzheimer's disease comprising determining the location and amount of amyloid plaques in the brain associated with Alzheimer's disease with SQUID imaging of a subject's head after the subject having been administered a plurality of superparamagnetic nanoparticles. The nanoparticles include an iron-containing core, a coating that allows passage of the nanoparticle across the blood-brain barrier, and a probe that is conjugated to the superparamagnetic nanoparticle for locating a superparamagnetic nanoparticle to a target associated with Alzheimer's disease. The SQUID imaging comprises magnetizing the plurality of superparamagnetic nanoparticles using external magnetic coils. The emitted decaying fields from only the superparamagnetic nanoparticles attached to the target and not from unattached superparamagnetic nanoparticles are measured to obtain magnetic field measurements. The location and quantity of the target in the brain is determined from the magnetic field measurements.

In yet another embodiment, an in-vivo method of treating Alzheimer's Disease comprises administering to a subject a plurality of superparamagnetic nanoparticles comprising an iron-containing core, a physiologically acceptable coating, a probe conjugated to the superparamagnetic nanoparticle for localizing the superparamagnetic nanoparticle to the target and a composition conjugated to the superparamagnetic nanoparticle that treats the target when the superparamagnetic nanoparticle is bound to the target. A rare earth magnet having strongly divergent magnetic fields is applied against the head of the subject at the location of the target in the brain to be treated to concentrate the number of superparagmagnetic particles at the target.

It is an object of the present invention to identify in-vivo Aβ plaques and/or neurofibrillary tangles using functionalized SPIONs that localize to a target associated with neurodegenerative disease of the brain It is another aspect of the present invention to SQUID image and distinguish bound functionalized SPIONs from unbound functionalized SPIONs.

Another aspect of the present invention provides for diagnosis of various nervous system-related disorders in mammals, preferably humans.

It is another object of the present invention to provide an inexpensive method to detect plaques in the brain. More particularly, the present invention relates to the use of such methods and compositions for the diagnosis, prognosis, and monitoring response to therapy of Alzheimer's disease, and for screening and evaluation of potential drugs for the treatment of Alzheimer's disease.

Another aspect of the present invention provides for a method to monitor subjects receiving therapy for treatment of a neurodegenerative disease and for drug effectiveness during development and usage.

One aspect of the present invention provides a method of monitoring change in the content in the brain.

Another aspect of the present invention provides for an improved method of delivery of drugs in the brain to treat AD.

Yet another aspect of the present invention provides for targeting of therapeutic agents to plaques associated with AD to thereby decrease the amount of drugs required for treatment. A substantial reduction in the amount of drug needed is obtained with resulting decrease of side effects compared with an injection of non-targeted anti-plaque drugs.

It is yet another aspect of the present invention to concentrate drugs or pharmaceutical compositions at plaque sites by applying strong external magnetic fields at sites identified by biomagnetic localization.

It is yet another object of the present invention to define the extent and overall number of plaques or other neurodegenerative molecules per unit area under the skull rather than precisely localize the individual plaques.

It is still another object of the present invention to provide a means of detecting in-vivo neurodegenerative disease with no radiation or high magnetic fields.

Another aspect of the present invention provides that nanoparticles may be used with many different molecules for specific targeting of sites by small molecule receptors which are specific to certain types of cells, amyloid plaques or other neurodegenerative diseases.

Another aspect of the present invention provides for detection of neurodegenerative disease in-vivo with injection of only minute amounts of superparamagnetic nanoparticles many orders of magnitude below toxicity limits of 5 mg/kg body weight and less than currently used for contrast agents in MRI studies of anatomical imaging of other organs.

Another aspect of the present invention provides for versatility of the superparamagnetic nanoparticle molecular coatings which offers a range of research opportunities in detection and identification of lesion types, early in-vivo detection of amyloid plaques and other neurodegenerative molecules, delivering and magnetically concentrating drugs at locations identified by the targeting agents to destroy these same molecules, and the capability of using RF fields to heat and destroy these same molecules at the locations identified by the targeting molecules and the biomagnetic sensor.

Magnetic concentration increases the amount of drugs delivered to the sites where plaques are to be destroyed while simultaneously reducing side effects of these drugs due to fewer drugs being required and fewer drugs invading unwanted sites in the body.

Additional objects and advantages of the present invention will be apparent in the following detailed description read in conjunction with the accompanying drawing figures.

DETAILED DESCRIPTION OF THE INVENTION

As used herein "a" means one or more.

As used herein "agent" means a drug or biologic useful for treating neurodegenerative disease of the brain.

As used herein "SPION" means superparamagnetic iron oxide nanoparticle and is used interchangeably with nanoparticle and superparamagnetic nanoparticle or magnetic nanoparticle.

As used herein "subject" can be either human or non-human animal, preferably mammalian.

As used herein SQUID means superconducting quantum interference device.

As used herein AD means Alzheimer's Disease.

As used herein target means AβPP, Aβ, tau, plaque, neurofibrillary tangle or a combination thereof.

According to one embodiment of the present invention, SPIONS functionalized to detect AD plaques, neurofibrillary tangles or other neurodegenerative pathophysiology in the brain are delivered to the subject. The SPIONS cross the blood-brain barrier and localize to the plaque, neurofibrillary tangles or other neurodegenerative pathophysiologies in the brain.

The localized SPIONS can be detected by sensitive magnetic sensors by measuring remanence magnetic fields as a function of time.

Figure 1:
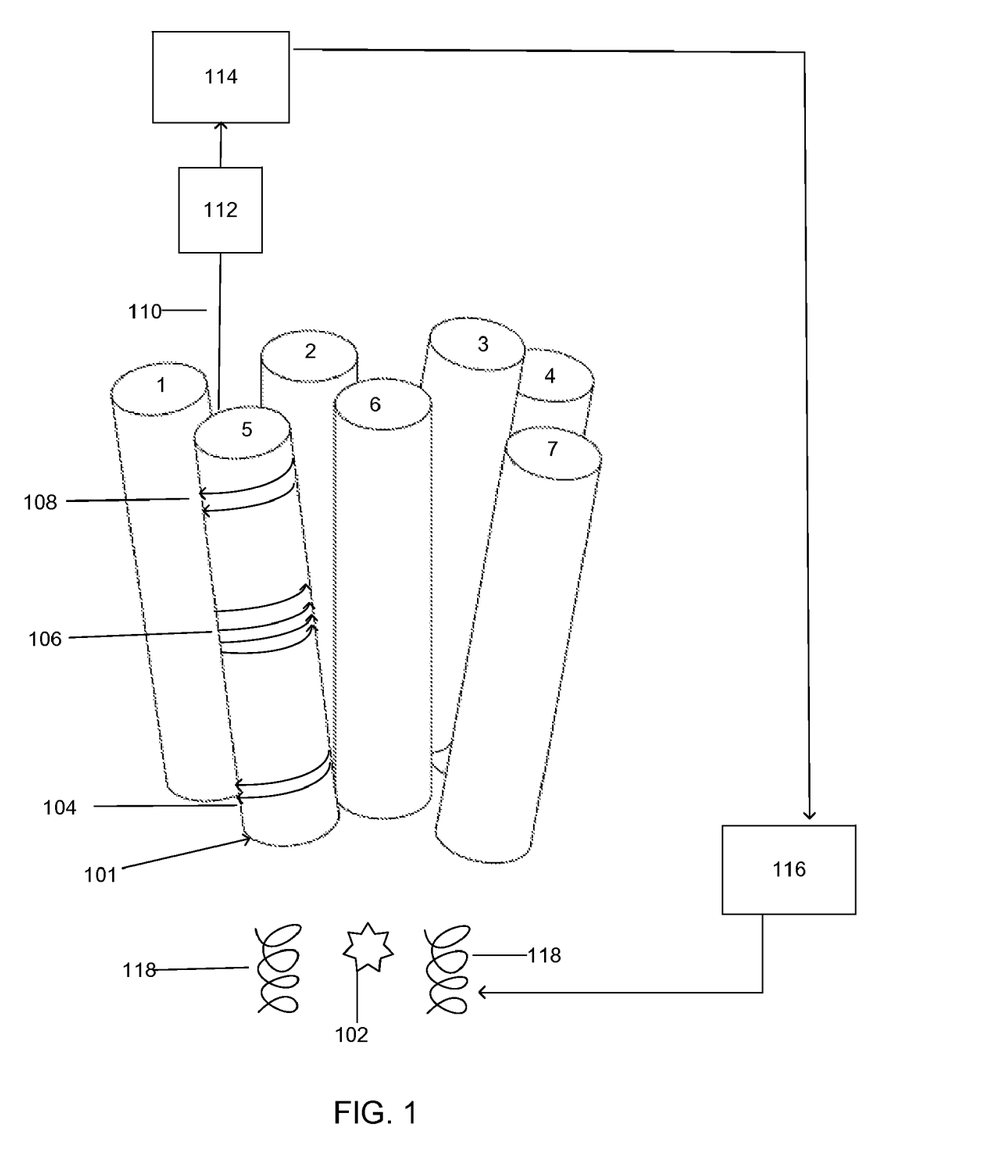
FIG. 1 illustrates a gradiometer according to one embodiment of the present invention.

Referring now to FIG. 1, one embodiment of a multichannel SQUID sensor system is illustrated. Gradiometer 101 comprises 2 loops of wire at 104, and 108 wound in the same direction while there are 4 loops of wire at 106 that are looped in the opposite direction wherein any current induced in the wire 106 is opposite to the current in 108 and 104. The arrangement of the gradiometer is to sense a source, whose strength falls off rapidly with distance, close to the sensor where the field in coil 104 will be larger than in coil 106 and still larger than the field in coil 108 resulting in a net current through the system of coils. Sources far away will produce uniform fields in all coils and result in a net cancellation of the total current. Wire 110 is in communication with SQUID 112 and conducts signals detected by gradiometer 101 from source 102 after source 102 has been magnetized by coil 118 upon receiving a magnetizing pulse from current generator 116. The SQUID 112 converts the magnetic fields to voltages. Processor 114 converts the voltages to digital forms for processing in a computer. While the present embodiment illustrates a seven gradiometer sensor system, the sensor system is not limited thereto as a sensor with four or more gradiometers as suitable. However, in general a minimum of four measurements are required to determine the vector components to localize a single magnetic source.

Figure 2:
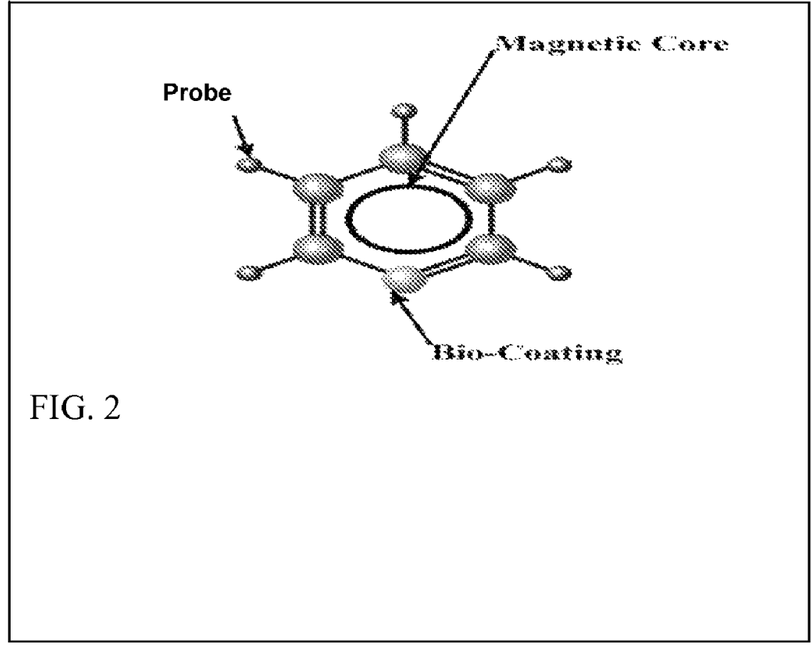
FIG. 2 illustrates a superparamagnetic nanoparticle having a biocompatible coating and conjugated to a probe.

Referring now to FIG. 2, a superparamagnetic nanoparticle with bio-coating and attached probe is illustrated as an example of a functionalized superparamagnetic iron oxide nanoparticle (SPION). The probe may be various forms of mAbs including, for example, mABβ1-42, mAβ-7, IgG1, IgG2a, and IgG2b. Anti Aβ antibodies are from Covance, Princeton, N.J. Unlabelled anti Amyloid antibodies are from EMD Chemicals Inc., Gibbstown, N.J. Anti Tau Antibodies are from Thermo Fisher Scientific Inc., Waltham, Mass. The coating is applied to the nanoparticle to cover partially or completely the entire nanoparticle.

Highly sensitive multichannel SQUID sensors have been used to measure the early stages of disease including cancer and transplant rejection. Flynn et al, *Use of a SQUID Array To Detect T-cells With Magnetic Nanoparticles In Determining Transplant Rejection*, Journal of Magnetism and Magnetic Materials, 311, p 429 (2007).

Applicant has measured the magnetic field from live lymphocyte cells targeted with functionalized SPIONS having an amplitude of 420 pT (picoTesla) using one embodiment of the sensor system. The sensitivity of one embodiment of the instrument used for these results without a shielded room is noise level is ~1 pT but may be improved to operate at 0.1 pT sensitivity by minimizing external noise sources and sensor response to the magnetizing pulse. Cell detection sensitivity can be increased to less than 1,000 cells at depths of 4 cm in the body.

Figure 3:
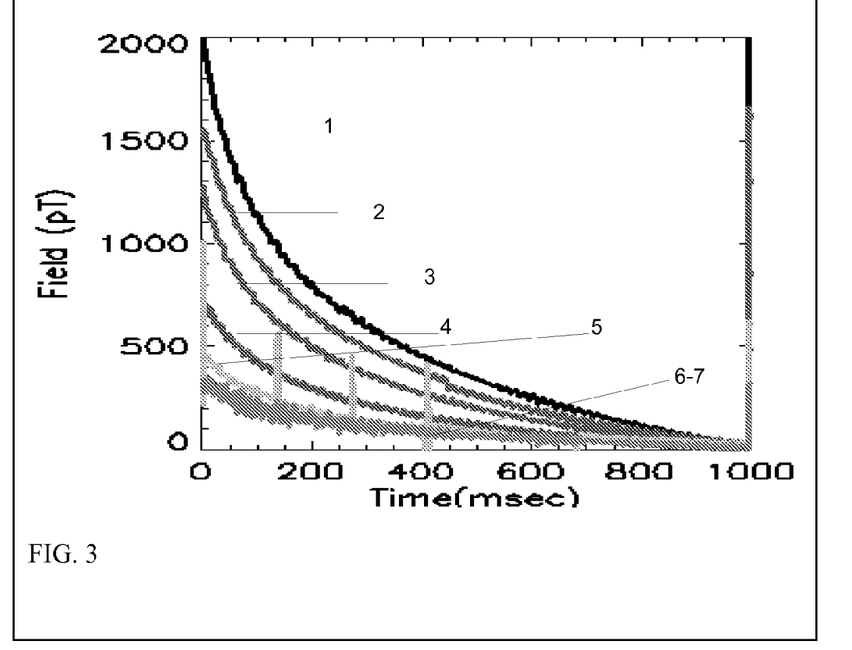
FIG. 3 illustrates a curve of measured magnetic field measured over time which is emitted from superparamagnetic nanoparticles attached to live cells through the action of specific antibodies, after application of a magnetizing field.

Referring now to FIG. 3, the results of magnetic field measurements obtained from four million live leukemia cells, with 20,000 magnetic nanoparticles attached to each cell through the action of specific CD3 antibodies is illustrated. The decaying remanence field is seen in all 7-channel (1-7) SQUID channels from a source of SPIONs coupled to Jurkat Cells conjugated with CD3 antibodies.

Figure 4:
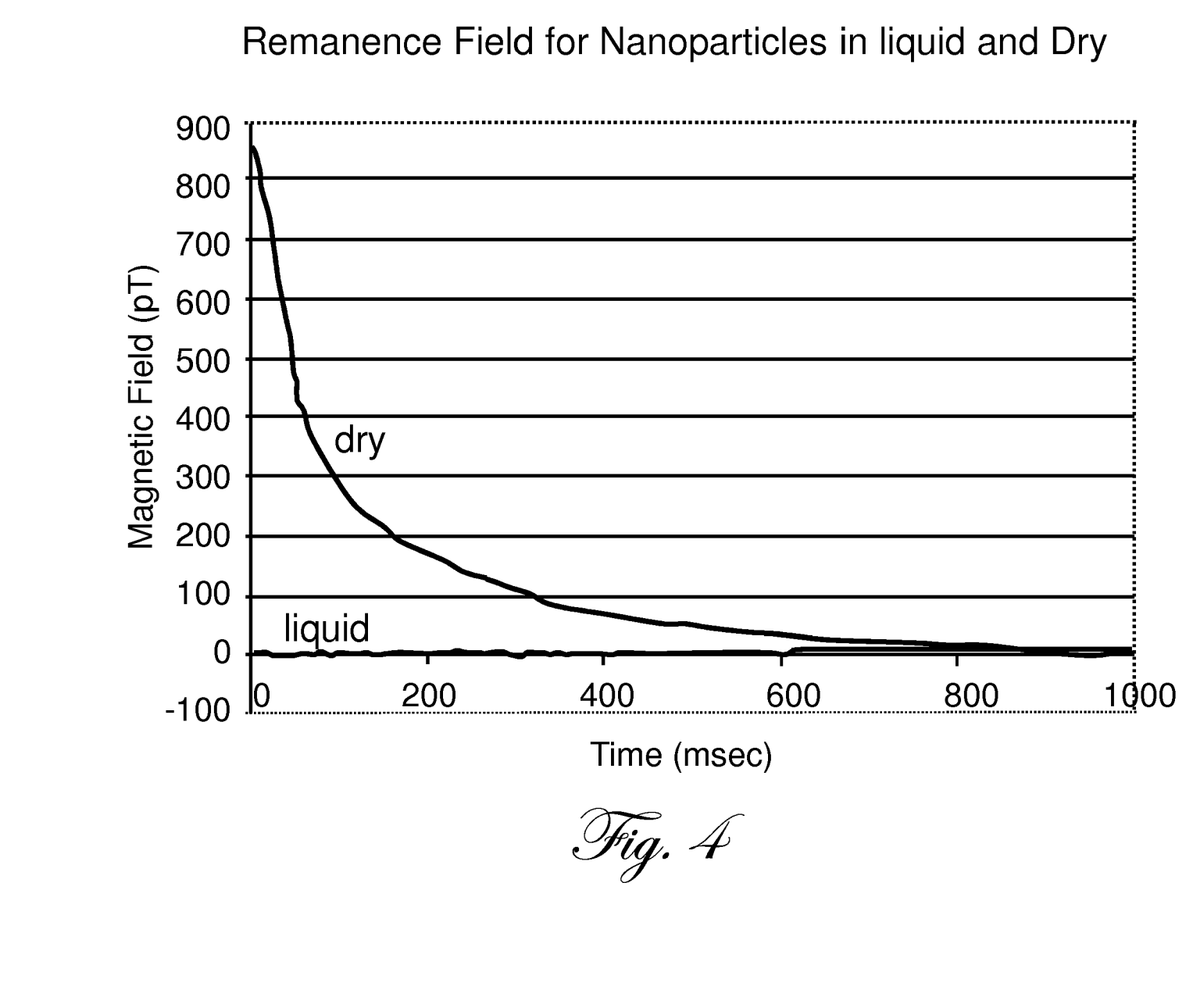
FIG. 4 illustrates a magnetic field from superparamagnetic nanoparticles coupled to live cells (upper curve) and from uncoupled particles (flat curve).

The fields are measured over several seconds, a time sufficient to measure all fields from bound particles. Fields from unbound particles decay too rapidly to be observed as shown in FIG. 4, a feature that provides optimal signal-to-background of targeted molecules versus nanoparticles that have not found targets. The measurements may be repeated multiple times and averaged to increase the accuracy of the measurement.

Figure 5:
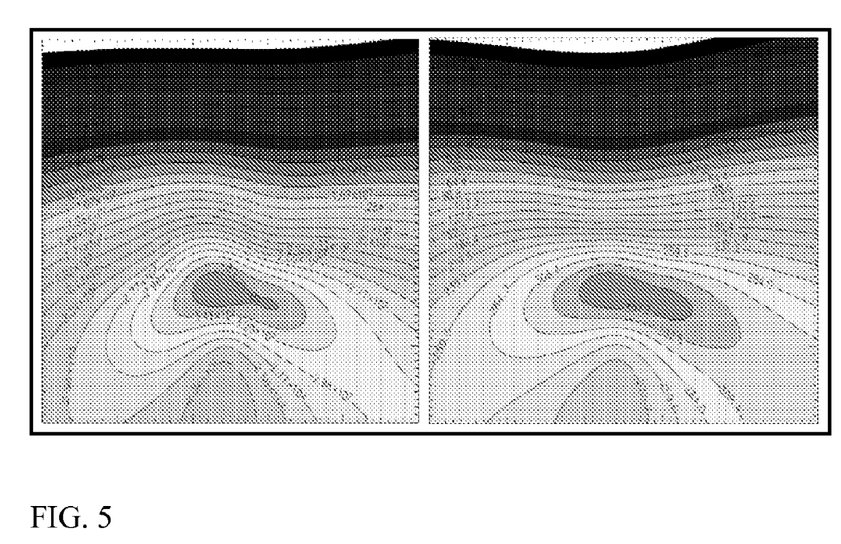
FIG. 5 illustrates magnetic contour lines of data from live cells compared to a theoretical prediction of these fields giving the location of the SPIONs localized to a target.

Referring now to FIG. 5, the measured and calculated field distributions for a group of living cells targeted by functionalized SPIONS are shown in the magnetic contour fields. The probe that targets the SPION to the cells is an antibody.

The blood-brain barrier (BBB) is a biological barrier that arises in the form of tight junctions between epithelial cells and impedes the uptake of many vascularly injected agents. Nanotechnology based systems have surprising efficacy in crossing the BBB and this crossing may be further enhanced by increasing the endothelial vascular permeability using a co-administration of polyethylene glycol or a bradykin antagonist. SPIONs coated with β-peptides such as putrescine amyloid-β are known to penetrate the blood-brain barrier. Poduslo, J. F., et al, *Molecular Targeting of Alzheimer's Amyloid Plaques for Contrast-Enhanced Magnetic Resonance Imaging*, Neurobiology of Disease, 11, p 315 (2002); Suemoto, T. et al, *In-vivo labeling of amyloid with BF-108*, Neurosci. Res., 48, p 65 (2004); Klunk, W E, *Imaging brain amyloid in Alzheimer's disease with Pittsburgh compound-B*, Ann. Neurol. 55, p 306 (2004); Wadghiri, Y Z, et al, *Detection of Alzheimer's amyloid in transgenic mice using magnetic resonance microimaging*, Magn. Reson. Med. 50, p 293 (2003); Poduslo, J F, et al, *Molecular Targeting of Alzheimer's Amyloid Plaques for Contrast-Enhanced Magnetic Resonance Imaging*, Neurobiology of Disease, 11, p 315 (2002); Sipkins, D A, et al, *Detection of tumor angiogenesis in vivo by $\alpha_v\beta_3$-targeted magnetic resonance imaging*, Nature Medicine, 4, p 623 (2002)1; Lockman, P R et al *Nanoparticle technology for drug delivery across the blood-brain barrier*, Drug Dev. Incl. Pharm. 28 p 1 (2002); Lockman PR et al, *Brain uptake of thiaminie-coated nanoparticles*, J. Control, Release 93, p 271 (2003); Wu, J. et al, *Modulation of enhanced permeability in tumor by a bradykin antagonist, a cyclooxygenase inhibitor*, Cancer, Res. 58 p 159 (1998); Podulso, J. F. et al, *Design and chemical synthesis of a magnetic resonance contrast agent with enhanced in vitro binding, high-blood barrier permeability, and in vivo targeting to Alzheimer's disease amyloid plaques*, Biochemistry, 43, p 6064 (2004).

For detection of plaques in the brain, SPIONS of between about 20-30 nm, preferably about 25-28 nm, in diameter are conjugated to one or more specific probes, that bind to the target of interest, for example, the AD plaque or neurofibrillary tangles in the case of AD. For example, probes, include those disclosed by Schostarez and Chrusciel in U.S. Pat. No. 7,053,109 but are not limited thereto as anti-tau, anti-amyloid beta, oranti-amyloid-precursor protein beta antibodies are useful.

The functionalized SPIONs contain coatings that are compatible with human insertion and assist in penetrating the blood-brain barrier and are injected into the blood stream of the subject are directly into the brain. These coatings may include the use of diamine derivatives as a method of penetrating the barrier. Podulso, J. F. et al, *Design and chemical synthesis of a magnetic resonance contrast agent with enhanced in-vitro binding, high-blood barrier permeability, and in-vivo targeting to Alzheimer's disease amyloid plaques*, Biochemistry, 43, p 6064 (2004). Alternatively, the SPIONs may be coated with a carboxyl coating. However, the coatings are not limited to carboxyl coatings as other physiologically acceptable coatings include Polyethylene glycol, Dextran, streptavidin, biotin, Polyvinyl alcohol, apolipoprotein E, human serum albumin. The probes may be antibodies, peptides, proteins, Protein nucleic acid, DNA, RNA or chemical moieties such as Pittsburgh Compound or 2-(1-[6-(dimethylamino)-2-naphtyl]ethylidene)malononitrite, but are not limited thereto.

In one embodiment of the present invention the nanoparticles are Chemicell Simag-1411 nanoparticles. The iron oxide cores measured were about 25 nm in diameter with 50 nm hydrodynamic radius and provided good remanence field signals. These particles are polydisperse and this particle size represents only a fraction of the total particles present.

The study of the Chemicell particles included measurements of: (1) remanent fields as a function of magnetizing pulse time and amplitude, (2) remanent fields as a function of the medium of deposition, both dried and fluid, and (3) TEM measurements of their diameters.

The functionalized SPIONs are delivered to the brain exhibiting the pathophysiologic structure or molecule of interest via the vasculature, either cerebral or systemic. Sufficient time is allowed during which binding of the functionalized SPION with the target can occur prior to SQUID imaging, or the targeting can be monitored in real time following administration of the SPIONs.

Figure 6:
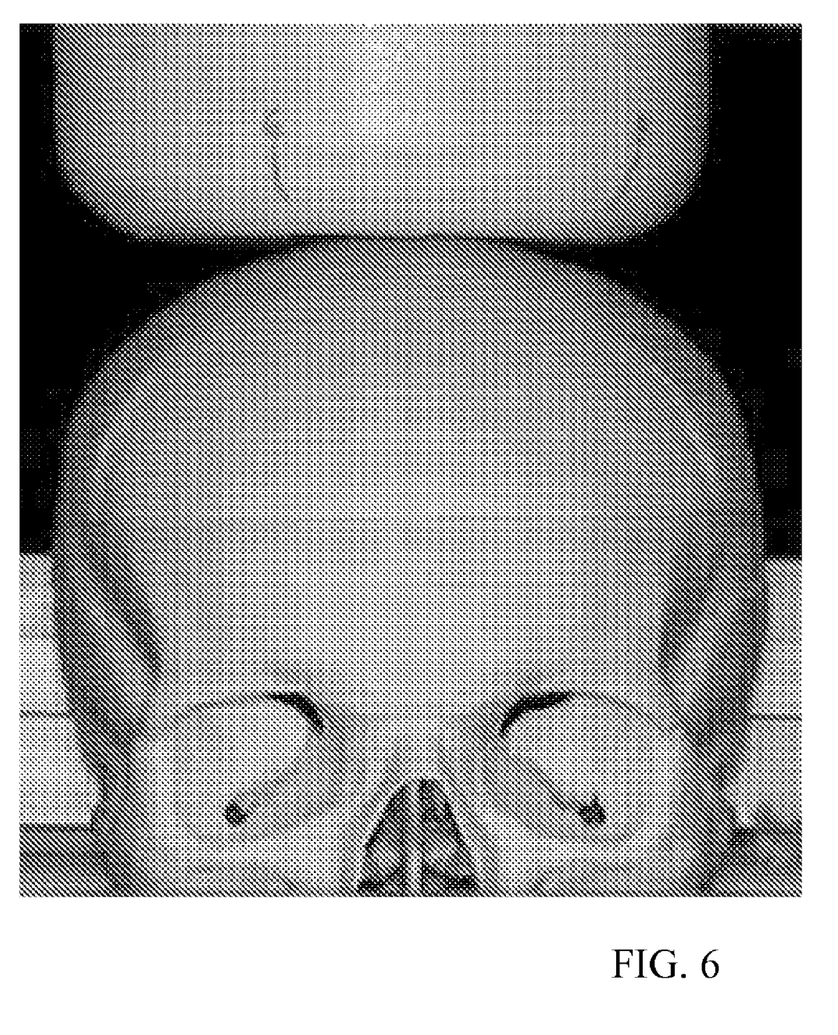
FIG. 6 illustrates a skull under a sensor system illustrating one embodiment of a measurement method for detecting plaques in Alzheimer's Disease through detection of superparamagnetic nanoparticles attached to plaques.

The human body, including the skull and brain, are transparent to low frequency magnetic fields. Referring now to FIG. 6, one embodiment of a sensor system containing the SQUIDs is placed over the head. According to FIG. 6, the human head, at one or more positions, is placed under a SQUID sensor array as illustrated. The array is located in a liquid helium dewar which is concave with a 16 mm spacing between the lip and the center of the dewar snout. The dewar is placed near or against the head.

A brief magnetizing field is applied to the functionalized SPIONs. The SQUID array detects the decaying remanence fields from the functionalized SPIONs bound to the target versus those functionalized SPIONs that are not after termination of the pulse. In some applications, the superparamagnetic nanoparticles attached to the target produce magnetic remanence fields lasting more than several hundred microseconds and less than tens of seconds.

The field amplitudes are extracted from the data after signal averaging and removal of line-frequency artifacts. A least-squares comparison is done between the field data and a theoretical source representing the known geometry of the sensor array and the total magnetic moment and location of the batch of functionalized SPIONs delivered.

The moment amplitude is divided by these previously measured moments of a single functionalized SPION to obtain the total number of SPIONs at the sources. The functionalized SPION is calibrated ex-vivo to a biological sample displaying a known number of events or targets, for example, a brain specimen from an Alzheimer patient. The number of functionalized SPIONs that bind to a plaque having delineated characteristics can be determined. From this determination and the number of SPIONs present, the number of plaques is determined.

The linearity of the response, saturation effects of SPIONs on the plaques, and incubation times per plaque are previously measured ex-vivo.

The technique can utilize minute amounts of functionalized SPIONs, consisting of iron oxide, similar to those used as MRI contrast agents and other biomedical applications. Golde, T. E. and Bacskai, B J, *Bringing amyloid into focus*, Nature Biotechnology, 23 p 552 (2005).

The utilized amount is an order of magnitude smaller than the current allowable 5 mg/Kg of body weight. These SPIONs would be injected into the subject where they would specifically target plaques, for example. However depending on the molecule that functionalized the SPION, the target may be tau tangles or other molecules or cells causing neurological diseases. The array of SQUIDs is then used to detect and image the targeted plaques.

Incubation dependence, saturation effects, and linearity of response are measured using various sample dilutions and incubation times.

The SPIONs that are not bound do not produce measurable fields, eliminating background signals from unbound particles circulating in the blood or elsewhere. This background suppression is a consequence of the two different relaxation times for the alignment of the particle's permanent magnetic moment following the application of a magnetizing pulse. The first relaxation time, referred to as "Brownian," applies to particles that are free to rotate in the viscous fluid in which they are suspended. This characteristic time is proportional to the volume of the particle, the viscosity of the suspending solution, and is inversely proportional to the temperature.

The second relaxation time applies when the physical particle cannot rotate such as, for example, if it were attached to the surface of a cell. In this case, the aligned electron spins comprising the magnetic moments have to overcome a spin-lattice interaction energy to change their orientations. Even though the single-domain crystal is hindered in its rotation, the collective moment due to the coherent alignment of hundreds of thousands of electron spins does realign. This Néel relaxation time has an exponential dependence on the volume of the magnetic core, the isotropy energy density of the crystal and on the inverse of the absolute temperature.

For magnetite superparamagnetic nanoparticles with a core diameter of about 24 nm, the Brownian relaxation time is of the order of 1 microsecond and Néel relaxation time of the order of 1 second. As a result, it is predicted only those particles that are bound to plaques are seen by the SQUIDs. The nanoparticles that have not attached to anything will not be seen as their relaxation times are much faster and not detected by the SQUID sensor. Thus, background from the unbound particles is eliminated, unlike the case when such magnetic particles are used as contrast agents in MRI.

Also, due to the strong size-dependence of the Néel mechanism, particles with even a slight difference in diameter will have noticeably different time constant. As a result, the relaxation of the net magnetic moment $\mu(t)$ of the nanoparticle ensemble will have non-exponential tail described by $$\mu(t)=a1n(1+b/t),$$

where t is time; a and b can be fit to the data. An exponential fit is used, for the very short times, to extrapolate into t=0, where the logarithmic relation is singular.

Because the relaxation times predicted by the Néel mechanism decrease drastically for the larger fields that are required to find the asymptotic induced magnetization, the duration of the magnetizing pulse can be fairly short. Normally pulses with about 0.3 to 1 second duration are used, collecting data for about 1 to 10 seconds after that. To increase the signal-to-background ratio, this pattern may be repeated about 10-25 times and the obtained signals averaged. A background run with no source is also made to remove the system's response to the pulsing. Although the pulse is terminated with a field drop to zero in less than about 3 msec, a delay of about 10-50 msec is utilized between the cessation of the magnetizing pulse and the beginning of the measurement period to permit induced currents in the system to die away. The magnetizing pulse from the Helmholtz coils produces a uniform field at the subject of about 38 Gauss.

In order to determine the number of the plaques that produce the signal seen by the SQUIDs, the number of nanoparticles bound to each plaque must be known, and also the magnetic moment of the nanoparticle itself. The latter quantity is determined as follows: The average magnetic moment $\mu_p$ of the nanoparticles contributing to the signal is obtained by fitting a normalized Langevin function to the "excitation curve" for a given sample. The Langevin function is the average value of the cosine of the angle between the magnetic dipole and the applied magnetic field as determined by classical Boltzmann statistics. The excitation curve is just the signal at a given time t measured by the SQUIDS as a function of the field B produced by the Helmholtz coils, starting at low levels and rising to the maximum possible field. The argument of the Langevin function, i.e., the coupling energy of the dipole to the field divided by the thermal energy, determines the shape of the curve, so by adjusting $\mu_p$ the fit can be optimized and the moment determined. Determination of the approximate moment of the particles is necessary in the interpretation of these measurements.

In estimating N, the number of particles contributing to the observed collective dipole moment of the polarized sample, the following representation for the signal measured by the SQUIDs is assumed:

$$S(t,B) = \mu(t) L(x),$$

with $x = \mu_p B/kT$. $\mu(t)$ represents the asymptotic limit of the signal (the collective moment of the aligned nanoparticles in the cell cluster) for very large B since $L(x)$ goes to unity. Thus $$N = \lim_{t \to 0} \mu(t)/\mu_p.$$

An exponential fit is used to extrapolate our data to the limit of t=0 at the end of the magnetizing pulse.

After permitting sufficient time for the particles to pass the blood-brain barrier into the brain and to attach to any amyloid plaques or other neurodegenerative targets that are present, a short pulse of a small external magnetic field, about 40G, is applied. This is produced by large external coils, referred to as Helmholtz coils, around the head. This magnetic field briefly aligns the magnetic moments of the injected nanoparticles that are in the brain. Results using this field of about 40 Gauss and for a pulse duration of about 0.30 seconds have shown that all of the nanoparticles are aligned with a magnetic moment representing about 60% of the maximum moment possible. However, a field of greater than about 35 Gauss is possible and will achieve greater than 60% of the maximum moment possible.

Specially developed software controls the data acquisition hardware and provides timing pulses to the Helmholtz coil power supply.

In one embodiment of the invention, the 7-channel SQUID sensor array is moved to several positions around the head and the measurements are repeated to obtain a wider distribution of locations of any neurodegenerative buildup in the brain. In other embodiments of the invention, larger numbers of sensors would be used to cover larger areas of the head.

An algorithm for extracting the total magnetic moment of the bound magnetic nanoparticles is applied to determine the distribution and strength of the magnetic fields in the sensor array. The magnetic moment of the bound particles is obtained by a least-squares computer algorithm that solves the inverse magnetic field problem using the constrained conditions imposed by the magnetizing field, the anatomy of the brain, and the geometry of the sensor system.

For the purposes of this invention, in-vitro measurements of the number of magnetic nanoparticles per amyloid plaque or other neurodegenerative feature or molecule is determined by separate SQUID sensor measurements in the laboratory preceding human subject measurements. The number of plaques or other targeted agents in the brain is determined by dividing the measured total magnetic moment from all of the attached nanoparticles observed in the brain by the number of nanoparticles per target as measured in the laboratory. From this calculation, the degree of neurodegenerative disease is determined as well as the locations in the brain affected.

The procedure to be followed is to make measurements at a number of positions of the sensor over the head and determine the overall strength of nanoparticles that have bound to plaques and give measurable remanence fields. Results of prior modeling and experimental results from brain phantoms then are used to obtain the total number of nanoparticles and subsequently, the number of plaques present.

Embodiments of the present system and method have important attributes including large signal-to-background ratios for detecting disease in-vivo compared to other potential detection methods, such as MRI or PET, due to biomagnetic measurable signals arising only from bound superparamagnetic particles and not those still in the surrounding blood vessels. This is shown in FIG. 5 where a large magnetic field is observed emanating from the nanoparticles that are bound to cells whereas the flat line at the bottom is from the same number of nanoparticles that are not bound to any cell or surface but are in suspension.

In addition to the probe used to locate the SPION to a target, additional molecules may be attached that specifically act against the target to provide therapeutic treatment. For example, when the target is an amyloid plaque, the additional molecule may be γ-secretase that is known to treat the plaque. This is referred to as multi-functional applications of the SPIONs.

The half-life of superparamagnetic nanoparticles in the body is determined by macrophage uptake and for 20-30 nm diameter magnetic nanoparticles is about 5 to 6 hours in blood at a dose of 300 μmoles Fe/kg after which they accumulate within cells of the mononuclear phagocytic system and are removed. Further, multiple molecular moieties of nanoparticles containing both targeting and plaque-destroying molecules can be used to introduce therapeutic agents to destroy plaques. Dual use of targeted molecules has numerous advantages and will provide a major treatment for removing plaques and a potential arrest of AD. The targeting molecule attaches to the plaque and also attaches directly to the destructive agent.

The present invention has been described in terms of preferred embodiments, however, it will be appreciated that various modifications and improvements may be made to the described embodiments without departing from the scope of the invention. The entire disclosure of all references, applications, patents, and publications cited above and/or in the attachments, and of the corresponding application(s), are hereby incorporated by reference.

I claim:

1. A method for in-vivo detection of neurodegenerative disease comprising:
   SQUID imaging of a subject's head after the subject having been administered superparamagnetic nanoparticles comprising an iron-containing core, a coating covering the core, and a probe molecule conjugated to the coating wherein the probe molecule locates the superparamagnetic nanoparticle to a target in the brain that is characteristic of the neurodegenerative disease;
   magnetizing the superparamagnetic nanoparticles using external magnetic coils with a field strength and application time that causes the superparamagnetic nanoparticles attached to the target to produce magnetic remanence fields lasting more than a microsecond but less than tens of seconds;

measuring the decaying remanence magnetic fields of the superparamagnetic nanoparticles attached to the target and not from unattached superparamagnetic nanoparticles to obtain magnetic field measurements; and detecting neurodegenerative disease from the magnetic field measurements and the magnetic properties of the superparamagnetic nanoparticles.

2. The method of claim 1 wherein the iron-containing core and coating covering the core are of a discrete size between about 20 and 30 nm.

3. The method of claim 1 where in the iron containing core and coating covering the core are of a discrete size between about 25-28 nm.

4. The method of claim 1 wherein the coating covering the core allows the superparamagnetic nanoparticles to pass through the blood-brain barrier.

5. The method of claim 1 wherein the probe that locates the superparamagnetic nanoparticle to the target in the brain is selected from a peptide, a protein, an antibody, a fAb or an agent.

6. The method of claim 1 wherein the neurodegenerative disease is selected from Alzheimer's Disease, multiple sclerosis, Parkinson's disease, Lewybody disease, and strokes.

7. The method of claim 1 further comprising determining the quantity of a the target in the brain from the magnetic field measurements.

8. A method as in claim 1, further comprising administering to the subject the superparamagnetic nanoparticles comprising an iron-containing core, a coating covering the core, and a probe molecule conjugated to the coating wherein the probe molecule locates the superparamagnetic nanoparticle to the target in the brain that is characteristic of the neurodegenerative disease, prior to SQUID imaging of the subject's head.

9. The method of claim 8 wherein administering superparamagnetic nanoparticles comprises injection of the superparamagnetic nanoparticles into the blood stream.

10. The method of claim 8 wherein administering superparamagnetic nanoparticles comprises injection of the superparamagnetic nanoparticles into the brain.

11. A method for in-vivo detection of Alzheimer's Disease comprising: determining the location and amount of amyloid plaques in the brain associated with Alzheimer's Disease comprising:

SQUID imaging of a subject's head after the subject having been administered a plurality of superparamagnetic nanoparticles comprising an iron-containing core, a coating, and a probe that is conjugated to each superparamagnetic nanoparticle for locating each superparamagnetic nanoparticle to a target comprising amyloid plaque;

wherein SQUID imaging comprises magnetizing the plurality of superparamagnetic nanoparticles using external magnetic coils with a field strength and application time that causes each of the superparamagnetic nanoparticles attached to the target to produce magnetic remanence fields lasting more than a microsecond but less than tens of seconds; measuring the emitted decaying fields from only those superparamagnetic nanoparticles that have attached to the target and not from those superparamagnetic nanoparticles that have not attached to the target to obtain magnetic field measurements;

determining the location and quantity of the target in the brain from the magnetic field measurements; and detecting Alzheimer's Disease from the location and quantity of the target in the brain.

12. The method of claim 11 wherein the iron-containing core and the coating are of a discrete size between about 20 and 30 nm in size.

13. The method of claim 11 wherein the iron-containing core and the coating are of a discrete size between about 25 and 28 nm in size.

14. The method of claim 11 wherein the coating allows the superparamagnetic nanoparticle to pass through the blood-brain barrier.

15. The method of claim 11 wherein the probe binds to the amyloid plaque and is selected from a peptide, a protein, an antibody, a fAb, or an agent.

16. A method as in claim 11, further comprising administering to the subject the plurality of superparamagnetic nanoparticles comprising an iron-containing core, a coating, and a probe that is conjugated to each superparamagnetic nanoparticle for locating each superparamagnetic nanoparticles to the target associated with Alzheimer's Disease, prior to SQUID imaging of the subject's head.

17. The method of claim 16 wherein administering superparamagnetic nanoparticles comprises injection of the superparamagnetic nanoparticles into the blood stream.

18. The method of claim 16 wherein administering superparamagnetic nanoparticles comprises injection of the superparamagnetic nanoparticles into the brain.

* * * * *